US008721331B2

(12) United States Patent
Raghuprasad

(10) Patent No.: US 8,721,331 B2
(45) Date of Patent: May 13, 2014

(54) ORAL TRANSMUCOSAL DRUG DELIVERY DEVICE

(76) Inventor: Puthalath Koroth Raghuprasad, Odessa, TX (US)

( * ) Notice: Subject to any disclaimer, the term of this patent is extended or adjusted under 35 U.S.C. 154(b) by 283 days.

(21) Appl. No.: 13/270,740

(22) Filed: Oct. 11, 2011

(65) Prior Publication Data

US 2013/0090627 A1 Apr. 11, 2013

(51) Int. Cl.

| | |
|---|---|
| ***A61C 17/00*** | (2006.01) |
| ***A61M 31/00*** | (2006.01) |
| ***A61F 13/20*** | (2006.01) |
| ***A61J 7/00*** | (2006.01) |

(52) U.S. Cl.

USPC ................. 433/80; 604/48; 604/11; 604/514; 604/77

(58) Field of Classification Search

USPC ................. 604/890.1, 891.1, 11, 514, 48, 77; 601/164; 600/237; 433/6, 8, 80; 128/859, 861

See application file for complete search history.

(56) References Cited

U.S. PATENT DOCUMENTS

| | | | | |
|---|---|---|---|---|
| 3,060,935 | A * | 10/1962 | Riddell | 604/514 |
| 3,688,406 | A * | 9/1972 | Porter et al. | 433/217.1 |
| 4,064,628 | A | 12/1977 | Weitzman | |
| 5,323,787 | A | 6/1994 | Pratt | |
| 6,068,475 | A | 5/2000 | Stoyka | |
| 6,322,360 | B1 * | 11/2001 | Burgio | 433/80 |
| 6,386,869 | B1 * | 5/2002 | Zegarelli | 433/80 |
| 6,660,029 | B2 | 12/2003 | VanSkiver et al. | |
| 7,029,690 | B1 | 4/2006 | Wehrli | |
| 7,661,430 | B2 | 2/2010 | Mason | |
| 8,105,079 | B2 * | 1/2012 | Farrell | 433/6 |
| 8,196,587 | B2 * | 6/2012 | Chodorow | 128/861 |
| 2008/0280251 | A1 | 11/2008 | Gallagher | |

FOREIGN PATENT DOCUMENTS

| | | |
|---|---|---|
| GB | 2464492 | 4/2010 |
| JP | 3018357 | 1/1991 |
| JP | 2008088095 | 4/2008 |
| KR | 20040086889 | 10/2004 |

* cited by examiner

*Primary Examiner* — Bhisma Mehta
*Assistant Examiner* — Bradley G Thomas, Jr.
(74) *Attorney, Agent, or Firm* — David L King

(57) ABSTRACT

A drug delivery device 10 has a support structure 20 and a medicine-laden member 100 affixed or otherwise attached to the support structure 20. The device 10 is sized to fit into the mouth and upon exposing the medicine-laden member 100 to saliva, medicaments 101 are released into the mouth. The drug delivery device 10 permits a new method of medication delivery. The method of oral transmucosal drug delivery has the steps of providing a drug delivery device 10 that fits into the mouth, the device 10 having a medicine-laden member 100; wearing the drug delivery device 10; activating release of medicine 101 by contact with saliva; and transmitting the released medicine 101 transmucosally to the bloodstream.

18 Claims, 8 Drawing Sheets

ORAL TRANSMUCOSAL DRUG DELIVERY DEVICE

TECHNICAL FIELD

This invention relates to an oral transmucosal drug delivery device that can be worn any time, concealed from view, preferably over the lower teeth and gums and provided with a removable medicine-laden member to deliver medicine directly into the blood stream of a patient through mucous membranes while bypassing the stomach and gastrointestinal tract.

BACKGROUND OF THE INVENTION

The most common way for administering medicine to patients is the oral route. While this route is convenient, there are some problems associated with it. For example, there is delay in absorption, and potential for side effects. Also, many drugs are absorbed abruptly, the blood levels rise quickly and just as quickly, the drug levels drop. This would lead to administering most drugs in multiple dosing to get some stability in the blood level. Sometimes this problem is circumvented by slowing the release of the drugs from the pills, in the stomach or intestines (extended or slow-release formulations).

Many other drugs are not suitable for the oral form as they may be rendered ineffective by the enzymes and the other components of the gastrointestinal juices. This is the case with all protein substances. Examples are Insulin and allergy shot antigens. These agents are therefore usually administered parenterally (by injection route).

The present invention provides a unique solution that will enable a variety of medicines to be self-administered transmucosally using a unique delivery system and device as described as follows. By formulating suitable carrier member (s) that will release drug(s) in a controlled, slow manner and then working along with higher or lower concentrations, any drug can be administered effectively. The current invention can make any drug available for absorption in a controlled manner, throughout the day and night. By making such agents available for rapid and direct absorption through the mucous membrane of the mouth, one can make all such drugs available for convenient administration. Thus, the avoidance of the pain as well as the logistics and expense of parenteral administration are special benefits of this new means of drug delivery.

SUMMARY OF THE INVENTION

A drug delivery device has a support structure and a medicine-laden member affixed or otherwise attached to the support structure. The device is sized to fit into the mouth and upon exposing the medicine-laden member to saliva, medicaments are released into the mouth. The drug delivery device permits a new method of medication delivery. The method of oral transmucosal drug delivery has the steps of providing a drug delivery device that fits into the mouth, the device having a medicine-laden member; wearing the drug delivery device; activating release of medicine by contact with saliva; and transmitting the released medicine to mucous membrane of the mouth.

The device is worn in the mouth preferably over the teeth and along the gums of a wearer. The device and more particularly, the support structure is a flexible open-support structure. The flexible open-support structure has two opposing bases, an inner base and an outer base. Each base extends along the length of the device and has a curvature to fit over the teeth and along the gums of a wearer of the device. The inner base fits between the teeth and the tongue while the outer base fits between the teeth and cheek and lips region of the mouth. A plurality of arch-shaped ribs extends from the inner base to the outer base joining the two bases to form the flexible open-support structure. The support structure has a means for receiving and holding the medicine-laden member for delivering a medicament transmucosally. The medicine-laden member is wetted by the production of saliva allowing the medicament to migrate into the mouth under the tongue where it is absorbed into the mucous membrane and transmitted into the bloodstream.

The flexible open-support structure has a connecting spine longitudinally extending between each arch rib connecting each rib along the length of the support structure.

The means for holding the medicine-laden member is a channel or groove extending along the length of the support structure. In a preferred embodiment the inner base has a recessed groove on a surface of the inner base extending along the length of the support structure, the groove forming the channel. In an alternative embodiment a flange is provided on the lower portion of the inner base which forms a groove or recess to hold the medicine-laden member.

Each inner base and outer base has a curved inner surface extending along the length of the structure, the combination of curved inner surfaces forms a flexible channel that on wearing, grips onto the outer surface of the teeth or gums. The support structure is preferably made of a flexible plastic or elastomer. The arched ribs are shaped to form a flexible spring-like enclosure of the inner base and opposing outer base, wherein upon inserting over the teeth, the bases open keeping the inner base and outer base in contact with the teeth and along the gums.

The plurality of arched ribs are positioned along rearward portions of the base structure which overlays the molars when worn. No arched ribs are located over regions which overlay the front teeth when worn; thus the inner and outer bases are concealed by the mouth and cheeks when the device is worn.

The medicine-laden member upon being wetted by saliva, releases medicaments that flow from the support structure under the tongue of the wearer.

The medicine-laden member for attachment in the support structure is made in the shape of a cord or string impregnated with a medicament. The medicine-laden member is made of a string or cord, the material of the string or cord being polystyrene or other natural or synthetic material suitable for being impregnated with a medicament. The medicament impregnated into the cord is releasable when exposed to saliva. The medicine is released when worn under the tongue region and delivered to the sublingual area. The types of drugs that may be administered transmucosally with the device: Insulin and its analogues; Anti-angina drugs such as the nitrates; Hormones such as the estrogens, androgens and progestogens; Pain controlling drugs such as the opiates, NSAIDs; Nicotine replacement drugs; Perhaps even vaccines (these are viral or bacterial products); and Any drug that needs repeated doses during the day.

BRIEF DESCRIPTION OF THE DRAWINGS

The invention will be described by way of example and with reference to the accompanying drawings in which.

DETAILED DESCRIPTION OF THE INVENTION

Figure 1A:
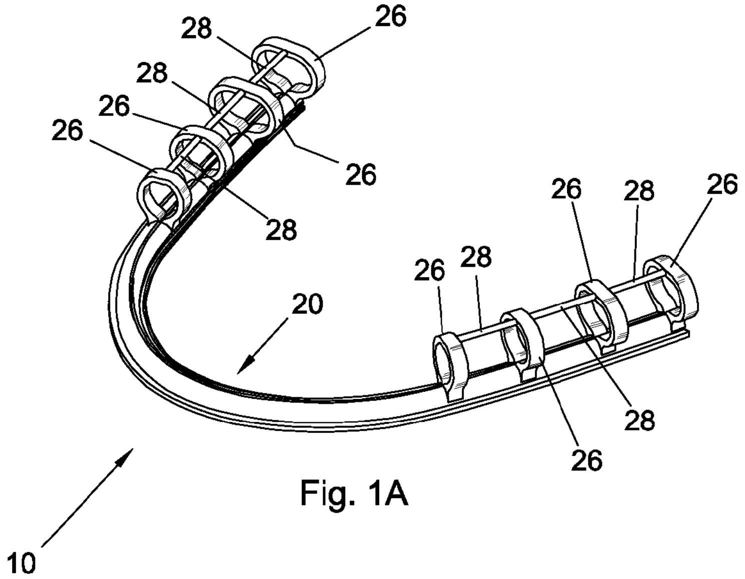
FIG. 1A is a first perspective view of the flexible open-support structure and medicine-laden member of the drug delivery device of the present invention.
Figure 1B:
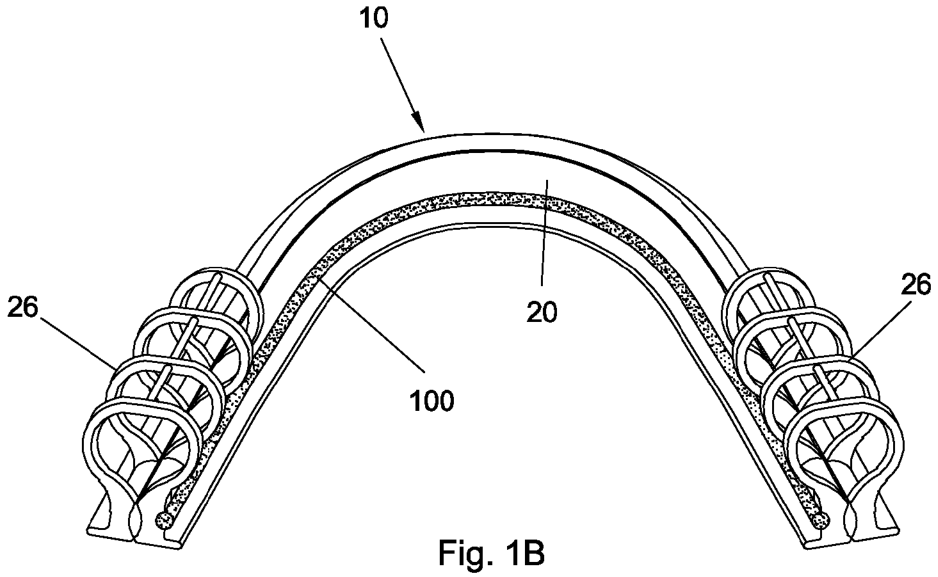
FIG. 1B is a second perspective view of the flexible open-support structure and medicine-laden member of FIG. 1A only looking from the open end of the device.
Figure 1C:
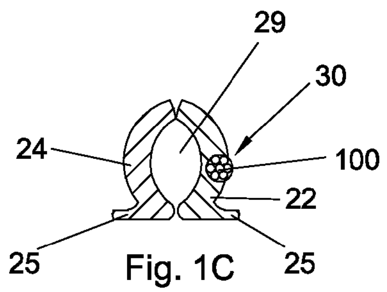
FIG. 1C is a cross sectional view of the support structure showing the two opposing inner and outer bases taken along section lines 1C-1C from FIG. 1A.

With reference to FIGS. 1A, 1B and 1C; the preferred embodiment drug delivery device 10 of the present invention is illustrated. As shown in FIG. 1A, the device 10 has a flexible open-support structure 20. As shown in FIG. 1C, a medicine-laden member can be affixed to an open channel or groove 30 of the device 10.

With reference to FIGS. 1A, 1B and 1C, the flexible open-support structure 20 is shown in greater detail. The flexible open-support structure 20 as shown has a pair of opposing bases 22 and 24; these opposing bases 22, 24 follow a curvature ideally suited to fit over a set of teeth either upper or lower. Connected to each base 22, 24 is a pair of arch-shaped ribs 26. The ribs 26 extend outward from the base in an arch shape and connect to the other base providing a secure spring-like connection between the two opposing bases 22 and 24. At the top surface of each arched rib 26 extends a longitudinally extending spine 28. The optional spine 28 extends along the length of the device in the location between the arched ribs 26 connecting each arched rib 26. Large open spaces exist between the arched ribs 26, the spine 28 and bases 22, 24. As shown, inside each base 22, 24 is an oval channel 29 as illustrated in FIG. 1A and in greater detail in FIG. 1C. The open channel 29 is composed of two parts formed by the contour of the inside surface of the base 22, 24 such that when the two opposing faced bases 22, 24 are in contact form a complete channel 29 as illustrated. The channel 29 flexes when placed in the mouth and fitted in place over the teeth creating a gripping or suction action to help hold the device 10 on the teeth and gums.

As shown in FIG. 1B from the ends of the bases, one can easily appreciate that the device 10 is held in a spring-like fashion wherein the channel 29 is maintained closed until the bases 22, 24 are separated apart.

On each side of the inner and outer bases at the bottom of the device 10 are a pair of feet 25. The feet 25 provide a flat surface and facilitate holding the device when placing it in the mouth.

As further shown in FIG. 1B, the ends of the device 10 are clearly visibly showing the medicine-laden member 100 affixed to the inner base 22 along an exterior surface. As better illustrated in FIG. 1C shown in a cross sectional view the medicine-laden member 100 is shown affixed in a groove 30. The groove 30 as shown is of circular cross section and extends along the length of the inner base 22. The opening of the groove 30 is large enough to accept the member 100 by flexing open as the member 100 is pressed into the groove 30. This enables the groove 30 at each end to grip onto the member preventing it from dislodging in the mouth when used by the wearer of the device 10.

Figure 1D:
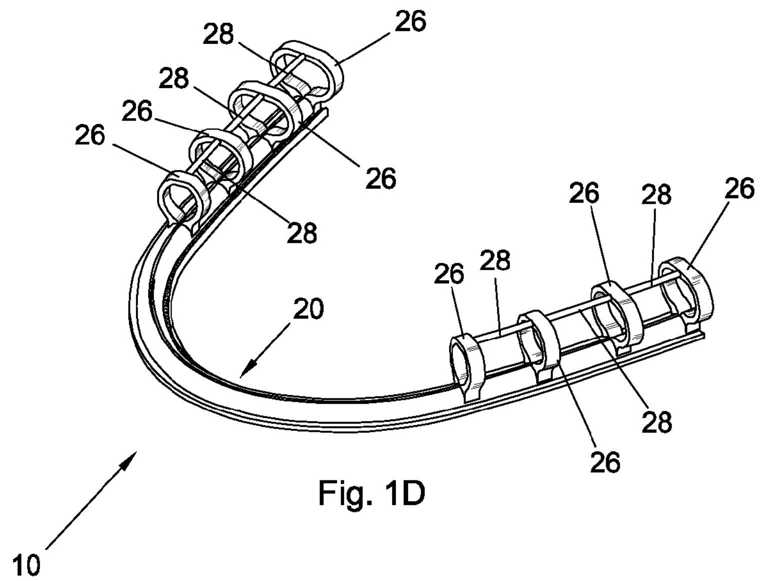
FIG. 1D is a first perspective view of an alternative embodiment device of the present invention.
Figure 1E:
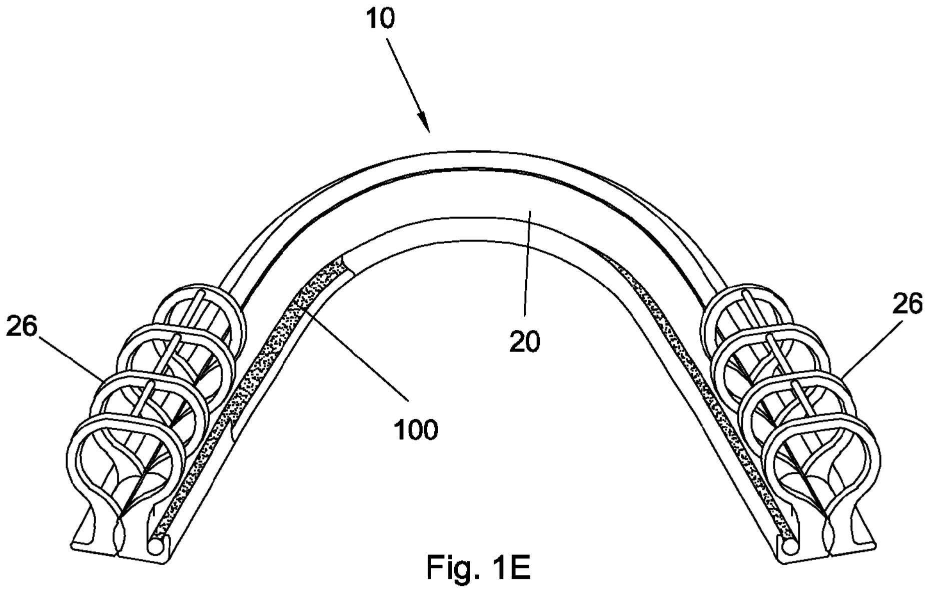
FIG. 1E is a second view of an alternative embodiment device of the present invention, looking from above the open ends of the device.
Figure 1F:
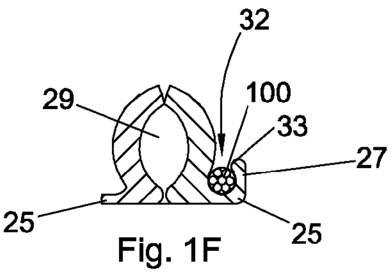
FIG. 1F is a cross sectional view of an alternative embodiment device of the present invention.
Figure 4:
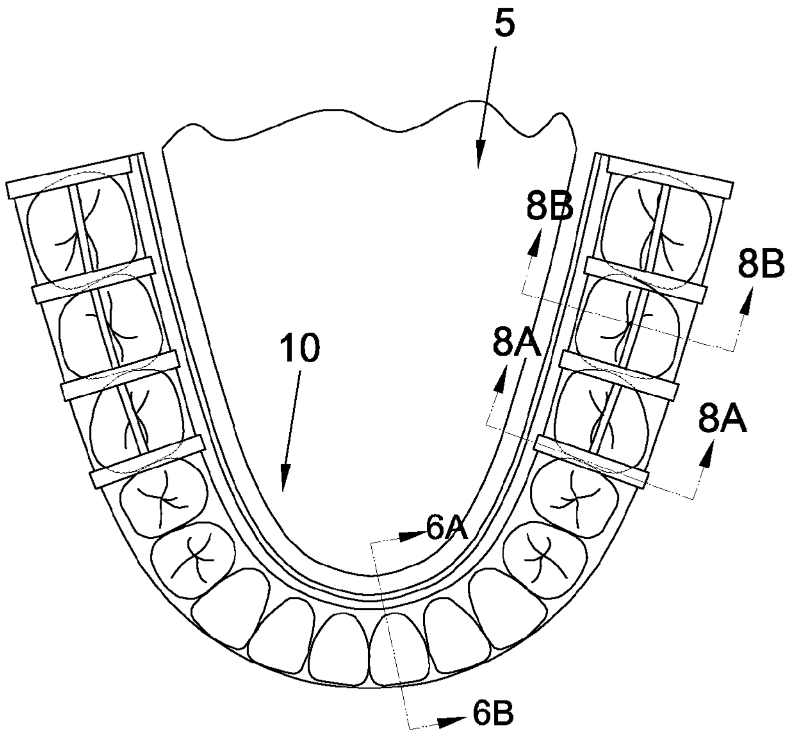
FIG. 4 is a plan view of the device mounted over the teeth.

With reference to FIGS. 1D, 1E and 1F; an alternative embodiment device 10 is illustrated. The alternative embodiment device 10 is identical to the preferred embodiment device shown in FIGS. 1A, 1B and 1C except that the groove 30 has been replaced by a flange 27 extending from the foot 25 along the inner base 22. The flange 27 and the inner base 22 form a groove or channel 32 into which the medicine-laden member 100 can be affixed. At an end of the flange 27 an enlarged projection 33 is shown. When placing a medicine-laden member 100 into the groove 32 the flange 27 flexes outwardly until the member 100 fully enters the channel or groove 32 wherein the flange 27 and projection 33 firmly hold the member 100 in place preventing it from dislodging. The reference numerals for the elements of both the preferred embodiment device 10 and the alternative device 10 are the same except for those features associated with securing the member 100. For illustrative purposes both embodiments are shown in FIGS. 5A-10B. In FIG. 4 only the preferred embodiment device is shown, it being understood the alternative device 10 fits over the teeth in an identical manner.

Figure 2A:
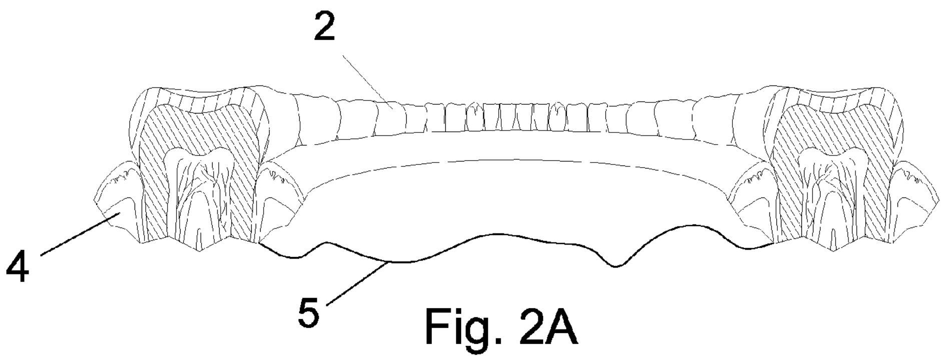
FIG. 2A is a perspective end view of a row of lower teeth.
Figure 2B:
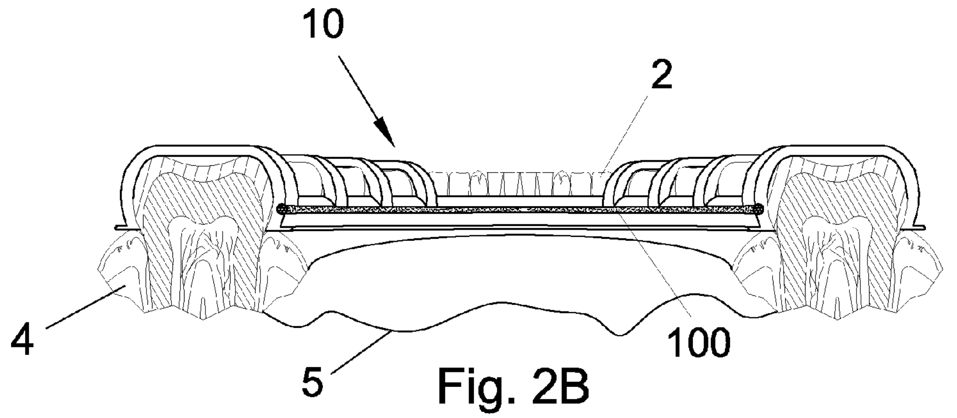
FIG. 2B is a perspective end view of the device according to the present invention mounted over the lower teeth.
Figure 2C:
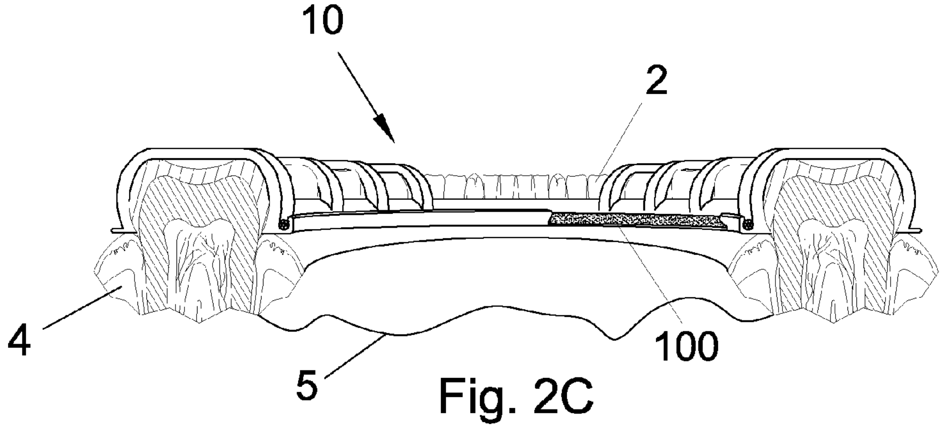
FIG. 2C is a perspective end view of the alternative device according to the present invention mounted over the lower teeth.
Figure 3:
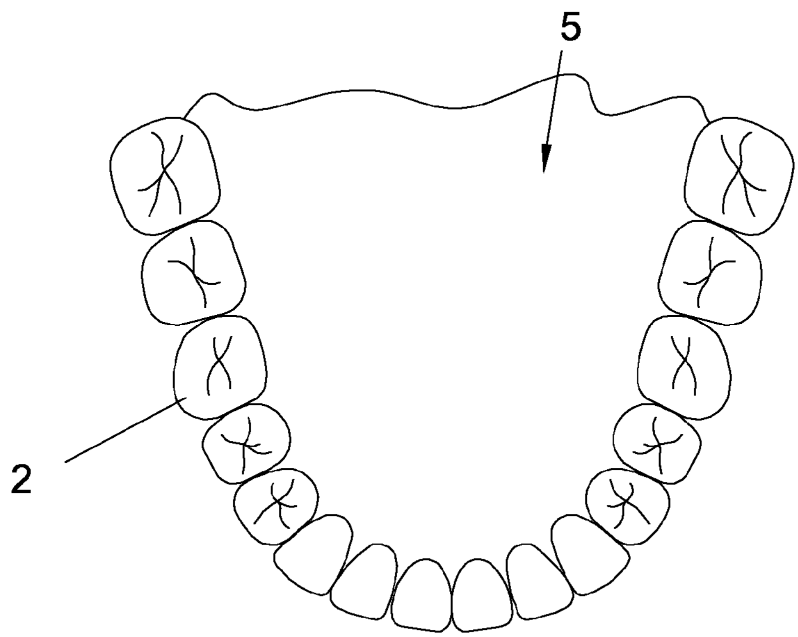
FIG. 3 is a plan view of a set of lower teeth.

In FIGS. 2A and 3 an end view of a bottom row of teeth 2 and a top view looking down on the bottom row of teeth 2 are shown respectively. In FIGS. 2B and 4 the device 10 is shown mounted on the teeth 2.

Figure 5A:
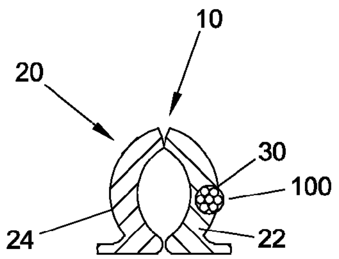
FIG. 5A is a cross sectional view of a version of the device.
Figure 5B:
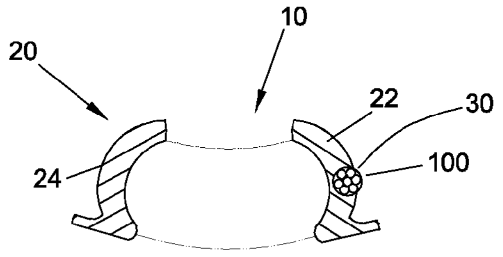
FIG. 5B is a cross sectional view of the device similar to FIG. 5A, but with the inner base and outer base pulled apart allowing both sides of the support structure to fit over the teeth.
Figure 5C:
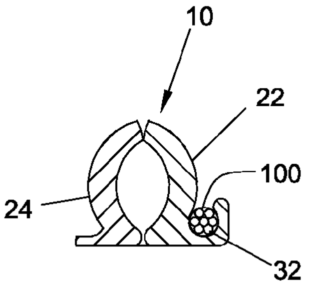
FIG. 5C is a cross sectional view of an alternative device.
Figure 5D:
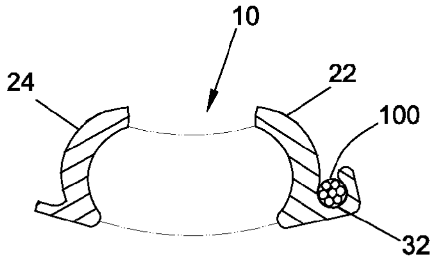
FIG. 5D is a cross sectional view of the alternative device similar to FIG. 5C, but with the inner base and outer base pulled apart allowing both sides of the support structure to fit over the teeth.

In FIGS. 5A and 5B the preferred device 10 is shown in a cross section and in FIGS. 5C and 5D the same views of the alternative device are shown. These views depict how the inner base 22 and outer base 24 are expanded to fit onto the teeth 2.

Figure 6A:
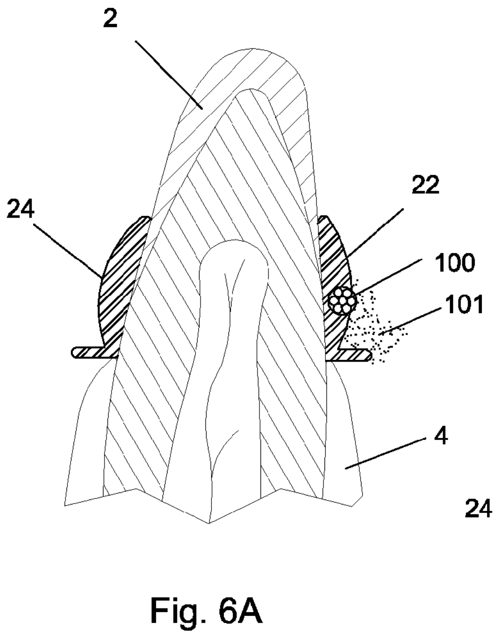
FIG. 6A is a cross sectional view of the device as it appears when mounted over the front teeth taken along lines 6-6 of FIG. 4.
Figure 6B:
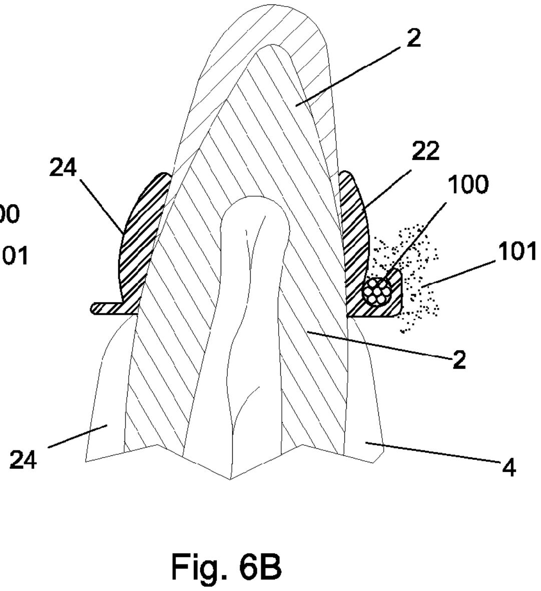
FIG. 6B is a cross sectional view of the alternative device as it appears when mounted over the front teeth.
Figure 7A:
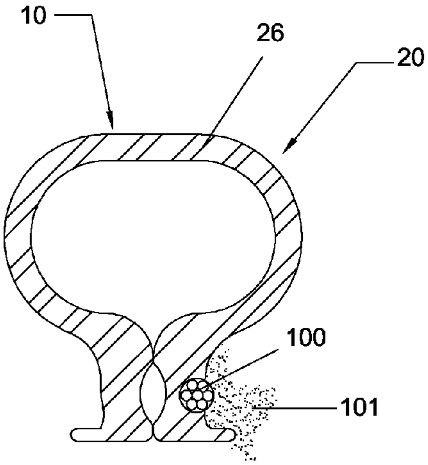
FIG. 7A is another cross sectional view taken along lines 7A-7A of FIG. 4 showing the device has a somewhat more open cavity for fitting on the molars.
Figure 7C:
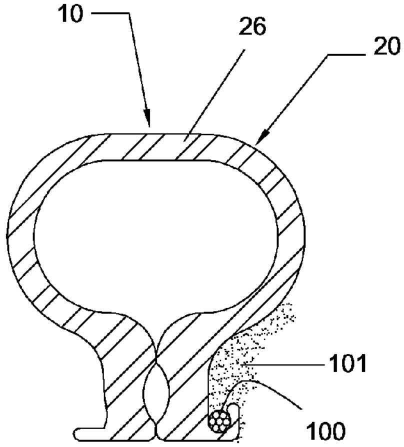
FIG. 7C is a cross sectional view showing the alternative device's appearance when open to wear over the rear teeth.
Figure 7B:
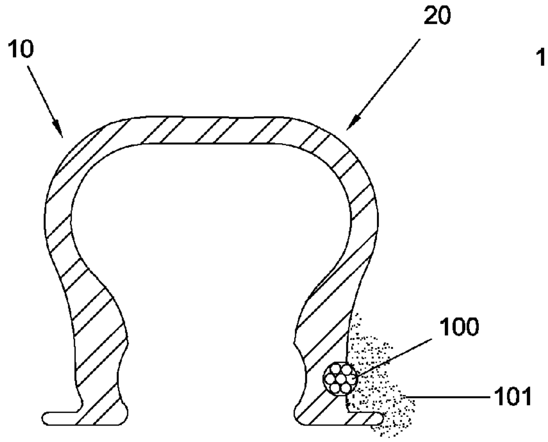
FIG. 7B is a cross sectional view showing the device's appearance when open to wear over the rear teeth.
Figure 7D:
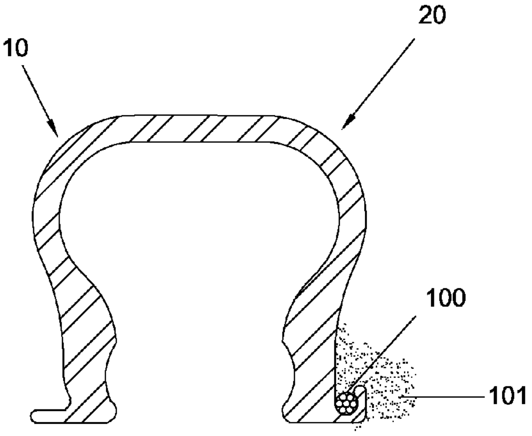
FIG. 7D is a cross sectional view showing the alternative device's appearance when open to wear over the rear teeth.
Figure 8A:
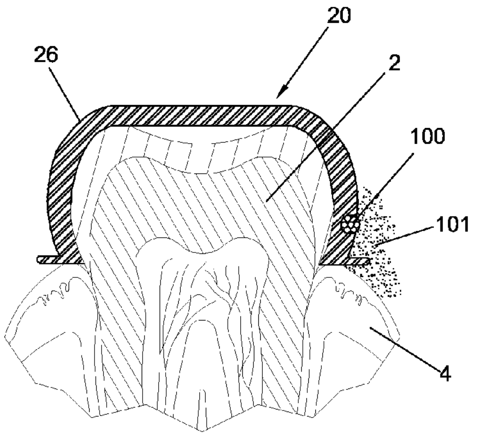
FIG. 8A is a cross sectional view showing the device mounted over a large molar tooth in the region of an arch rib taken along lines 8A-8A of FIG. 4.
Figure 8B:
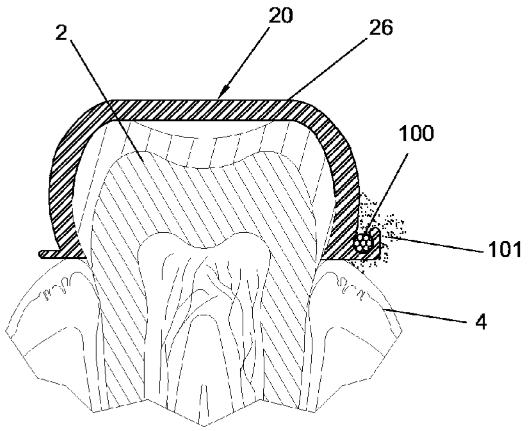
FIG. 8B is the same view as FIG. 8A in an open region between the arch ribs showing how the device contacts the teeth taken along lines 8B-8B of FIG. 4.
Figure 9A:
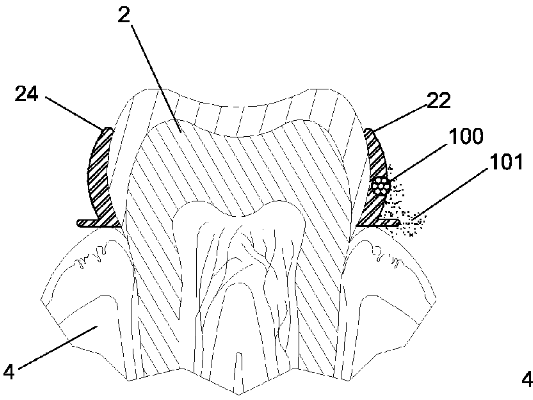
FIG. 9A is a cross sectional view showing the alternative device mounted over a large molar tooth in the region of an arch rib.
Figure 9B:
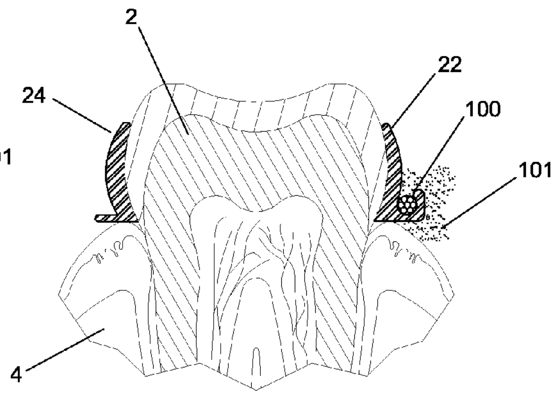
FIG. 9B is the same view as FIG. 9A in an open region between the arch ribs showing how the alternative device contacts the teeth.

In the cross sectional views of FIGS. 6A, 6B, 7A, 7B, 7C, 7D, 8A, 8B, 9A and 9B, the devices 10 of the preferred and alternative embodiment are shown with the medicine 101 being dispensed from the member 100. In FIG. 6A, the front portion of the device 10 is illustrated fitting over the front teeth 2 which are substantially narrower than the rearward-positioned molars. The teeth 2 and the device 10 extend down to the gums 4 providing a fit over the teeth 2 and along the gums 4 in this area. In FIGS. 7A-7D the teeth 2 are not shown. With reference to FIGS. 8A, 8B, 9A and 9B, showing the rear portion of the devices 10 when the bases 22, 24 are spread apart in such a fashion that the devices 10 can fit over the shallower molars 2 which are substantially wider, therefore creating a more open appearance of the devices 10. Again the devices 10 fit directly over the teeth 2 and along the gums 4 as illustrated. In this case, medicine 101 is shown as a dispersion spreading the medicine 101 downward past the gums 4 as the saliva activates release of the medicine 101 allowing it to migrate along the gums 4 and into a mucous membrane area under the tongue, (the tongue is not shown, to expose the mucous membrane area).

Figure 10A:
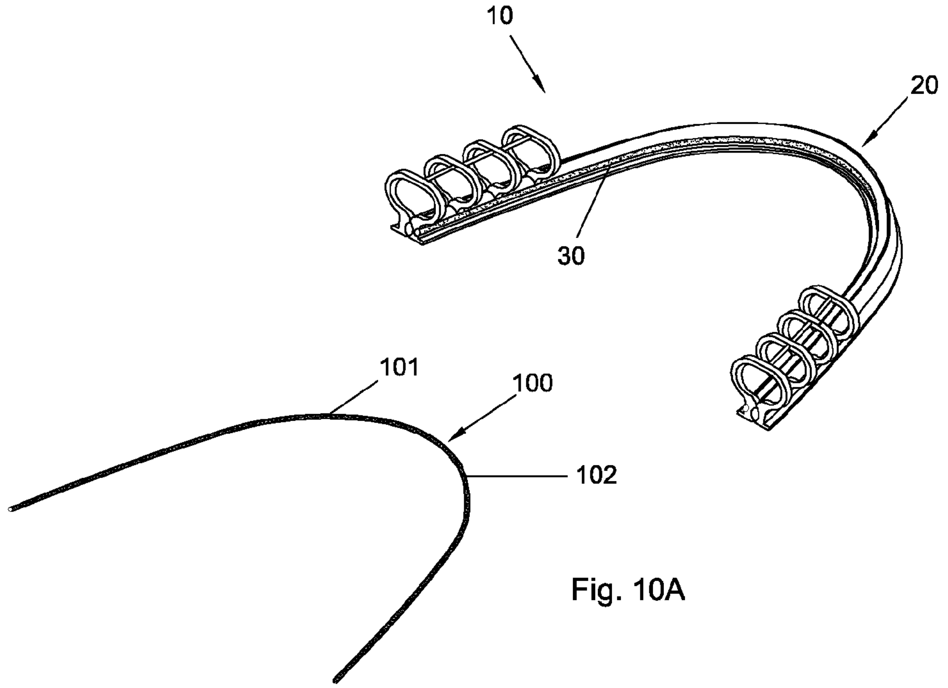
FIG. 10A is a perspective exploded view showing the device with the support structure and medicine-laden member shown removed therefrom.
Figure 10B:
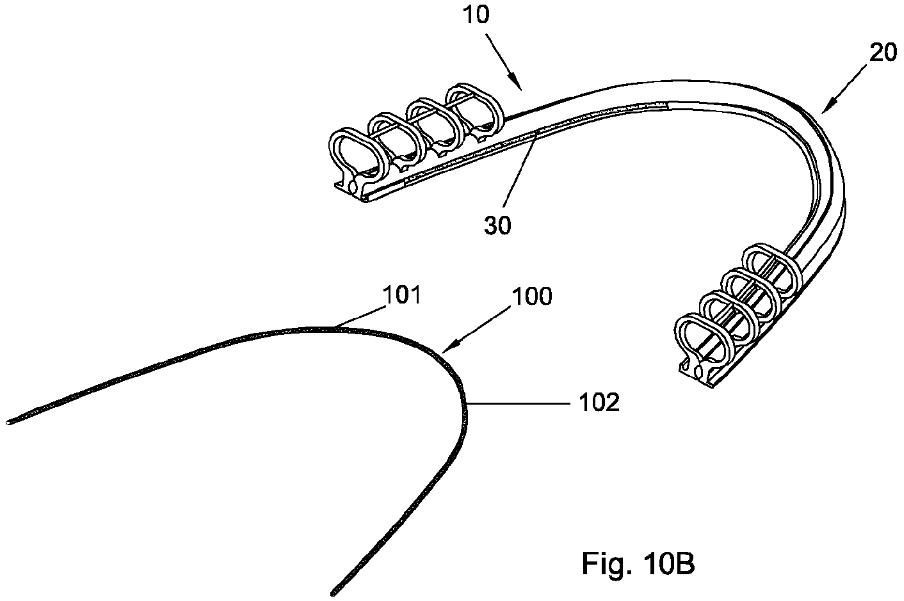
FIG. 10B is a perspective exploded view showing the alternative device with the support structure and medicine-laden member shown removed therefrom.

With reference to FIGS. 10A and 10B, the device 10 of the preferred and alternative embodiments is shown in exploded view. The medicine-laden member 10 being removed from the support structure 20. With particular reference to the medicine-laden member 100 it is shown formed as a string or cord 102 laden with medicine 101. The medicine-laden member 100 for attachment in the support structure 20 is made in the shape of a cord or string 102 impregnated with a medicament 101. The medicine-laden member 100 is made of a string or cord 102, the material of the string or cord being polystyrene or other natural or synthetic material suitable for being impregnated with a medicament 101. The medicament 101 impregnated into the cord 102 is releasable when exposed to saliva. The medicine 101 is released when worn under the tongue region and delivered to the sublingual membrane. The types of drugs 101 that may be administered transmucosally with the device: Insulin and its analogues; Anti-angina drugs such as the nitrates; Hormones such as the estrogens, androgens and progestogens; Pain controlling drugs such as the opiates, NSAIDs; Nicotine replacement drugs; Perhaps even vaccines (these are viral or bacterial products); and Any drug that needs repeated doses during the day. It is important to note the member 100 can be impregnated with more than one drug or medicament 101 in a combination. For example, an antihistamine and a decongestant or a blood pressure lowering medicine along with a cholesterol lowering drug could be combined. For that matter, the member 100 could be pharmaceutically prepared to match a specific patient by having a specific combination of prescribed medicines impregnated for a specific patient. In this manner, the patient simply wears the device and all required medicines can be delivered in a controlled manner without requiring multiple administrations of oral or injectables. This greatly simplifies the procedure and insures proper dosages and medicines are taken. One way to achieve multiple medicines is to have the member 100 comprised of two or more cords or threads 102 each having different medicaments 101 so these different drugs can be administered at the same time.

As illustrated, this device 10 is designed to be worn any time. It can be worn over a period of several hours due to the pliant nature of the open support structure 20. The device 10 is adapted to be minimally invasive and of such light weight that the wearer can wear it comfortably without hampering his or her ability to eat or talk. As shown, the device 10 is mounted preferably on the lower set or row of teeth 2. As shown, the device 10 provides an excellent means for providing prolonged treatment with otherwise injectable or erratically absorbed medicines. This is of particular value in that most medicaments cannot currently be provided or applied over a period of time. The present invention provides an ideal means for providing the medicaments over an extended period of time. This is particularly important as it makes it possible for the wearer to get an extended treatment heretofore unavailable. This feature is particularly useful when treating chronic conditions such as diabetes with insulin. Antibiotics and other medicines can be used with this device 10 which can make the treatment shorter in overall duration and more effective, possibly eliminating the need to administer the antibiotics systemically by way of pills taken orally or injections. The present invention, as designed is molded to the shape of the open support structure 20.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A concealed drug delivery device comprises:

a support structure;

a medicine-laden member affixed or otherwise attached to the support structure; and wherein the device is sized to fit into the mouth and upon exposing the medicine-laden member to saliva, medicaments are released into the mouth and placing the device in the mouth wherein the device is worn in the mouth over the teeth and along the gums of a wearer, and the support structure is a flexible open-support structure, the flexible open-support structure having two opposing bases, an inner base and an outer base, each base extends along the length of the device to ends inside the mouth when worn and has a curvature to fit over the teeth and along the gums of a wearer of the device, the inner base fits between the teeth and the tongue while the outer base fits between the teeth and cheek and lips region of the mouth, a plurality of arch-shaped ribs extend from the inner base to the outer base along each end of the open-support structure but do not extend beyond the location covering the pre-molars, joining the two bases to form the flexible open-support structure wherein the open support structure along the front teeth is hidden from view, wherein the support structure has a means for receiving and holding the medicine-laden member for delivering a medicament transmucosally, the means being located in the inner base wherein the medicine-laden member is wetted by the production of saliva allowing the medicament to migrate into the mouth.

2. The concealed drug delivery device of claim 1 wherein the flexible open-support structure has a connecting spine longitudinally extending between each arch rib connecting each rib along the length of the support structure.

3. The concealed drug delivery device of claim 1 wherein the means for holding the medicine-laden member is a channel extending along the length of the support structure.

4. The concealed drug delivery device of claim 3 wherein the inner base has a recessed groove on an outer surface of the inner base adjacent the tongue of the wearer, the recessed groove extending along the length of the support structure, the groove forming the channel.

5. The concealed drug delivery device of claim 4 wherein each inner base and outer base has a curved inner surface extending along the length of the structure, the combination of curved inner surfaces forms a flexible channel that on wearing grips onto the outer surface of the teeth or gums.

6. The concealed drug delivery device of claim 1 wherein the medicine-laden member upon being wetted by saliva releases medicaments that flow from the support structure under the movement of the tongue of the wearer.

7. The concealed drug delivery device of claim 1 wherein the plurality of arched ribs are positioned along rearward portions of the base structure which overlays the molars when worn.

8. The concealed drug delivery device of claim 7 wherein no arched ribs are located over regions which overlay the front teeth when worn.

9. The concealed drug delivery device of claim 8 wherein the inner and outer bases are concealed by the mouth and cheeks when the device is worn.

10. The concealed drug delivery device of claim 9 wherein the medicine-laden member is made of a string or cord, the material of the string or cord being polystyrene or other natural or synthetic material suitable for being impregnated with a medicament.

11. The concealed drug delivery device of claim 1 wherein the medicine-laden member for attachment in the support structure is made in the shape of a cord or string impregnated with a medicament.

12. The concealed drug delivery device of claim 11 wherein the medicament impregnated into the cord is releasable when exposed to saliva.

13. The concealed drug delivery device of claim 12 wherein the medicine is released when worn under the tongue region and delivered to the sublingual area.

14. The concealed drug delivery device of claim 1 where the medicine is any drug needing to be delivered in a controlled manner.

15. The concealed drug delivery device of claim 1 wherein the medicine-laden member is impregnated with a medicament including, but not limited to protein based drugs such as insulin and its analogues; anti-angina drugs such as the nitrates; hormones such as the estrogens, androgens and progestogens; pain controlling drugs such as the opiates, NSAIDs; nicotine replacement drugs; vaccines of viral or bacterial products; and any drug that needs repeated doses during the day.

16. A concealed drug delivery device comprises:

a support structure;

a medicine-laden member affixed or otherwise attached to the support structure; and wherein the device is sized to fit into the mouth and upon exposing the medicine-laden member to saliva, medicaments are released into the mouth and placing the device in the mouth wherein the device is worn in the mouth over the teeth and along the gums of a wearer, and the support structure is a flexible open-support structure, the flexible open-support structure having two opposing bases, an inner base and an outer base, each base extends along the length of the device to ends inside the mouth when worn and has a curvature to fit over the teeth and along the gums of a wearer of the device, the inner base fits between the teeth and the tongue while the outer base fits between the teeth and cheek and lips region of the mouth, a plurality of arch-shaped ribs extend from the inner base to the outer base along each end of the open-support structure but do not extend beyond the location covering the pre-molars' joining the two bases to form the flexible open-support structure wherein the open support structure along the front teeth is hidden from view, wherein the support structure has a means for receiving and holding the medicine-laden member for delivering a medicament transmucosally, the means being located in the inner base wherein the medicine-laden member is wetted by the production of saliva allowing the medicament to migrate into the mouth, wherein the support structure is made of a flexible plastic or elastomer and wherein the arched ribs are shaped to form a flexible spring-like enclosure of the inner base and opposing outer base, wherein upon inserting over the teeth, the bases open keeping the inner base and outer base in contact with the teeth and along the gums.

17. A method of oral transmucosal drug delivery comprises the steps of:

providing a concealed drug delivery device that fits into the mouth, the device having a medicine-laden member;

placing the device in the mouth wherein the device is worn in the mouth over the teeth and along the gums of a wearer, the device has a support structure that is a flexible open-support structure, the flexible open-support structure having two opposing bases, an inner base and an outer base, each base extends along the length of the device to ends inside the mouth when worn and has a curvature to fit over the teeth and along the gums of a wearer of the device, the inner base fits between the teeth and the tongue while the outer base fits between the teeth and cheek and lips region of the mouth, a plurality of arch-shaped ribs extend from the inner base to the outer base along each end of the open-support structure but do not extend beyond the location covering the pre-molars' joining the two bases to form the flexible open-support structure wherein the open support structure along the front teeth is hidden from view, wherein the support structure has a means for receiving and holding the medicine-laden member for delivering a medicament transmucosally, the means being located in the inner base wherein the medicine-laden member is wetted by the production of saliva allowing the medicament to migrate into the mouth;

wearing the drug delivery device;

activating release of medicine by contact with saliva; and transmitting the released medicine transmucosally to the blood stream.

18. The method of oral transmucosal drug delivery of claim 17 wherein the medicine-laden member is impregnated with a medicament including, but not limited to protein based drugs such as insulin and its analogues; anti-angina drugs such as the nitrates; hormones such as the estrogens, androgens and progestogens; pain controlling drugs such as the opiates, NSAIDs; nicotine replacement drugs; vaccines of viral or bacterial products; and any drug that needs repeated doses during the day.

* * * * *